United States Patent

Baldwin et al.

Patent Number: 5,382,587
Date of Patent: Jan. 17, 1995

[54] SPIROCYCLES

[75] Inventors: John J. Baldwin, Gwynedd Valley; David A. Claremon, Maple Glen, both of Pa.; Jason M. Elliott, Kent, Great Britain

[73] Assignee: Merck & Co., Inc., Rahway, N.J.

[21] Appl. No.: 85,573

[22] Filed: Jun. 30, 1993

[51] Int. Cl.[6] .................. A61K 31/445; C07D 211/06
[52] U.S. Cl. ........................................ 514/278; 546/17
[58] Field of Search .............................. 546/17; 514/278

[56] References Cited

U.S. PATENT DOCUMENTS

| 3,649,635 | 3/1972 | Cohen et al. | 546/18 |
| 3,686,186 | 8/1972 | Nadelson et al. | 546/17 |
| 3,980,655 | 9/1976 | Kunstmann et al. | 546/141 |
| 4,166,119 | 8/1979 | Effland et al. | 424/267 |
| 4,353,900 | 10/1982 | Clark | 424/248.54 |
| 4,420,485 | 12/1983 | Davis et al. | 424/267 |
| 4,544,654 | 10/1985 | Davey et al. | 514/210 |
| 4,629,739 | 12/1986 | Davey et al. | 514/605 |
| 4,650,798 | 3/1987 | Minami et al. | 514/277 |
| 4,788,196 | 11/1988 | Cross et al. | 514/252 |
| 4,797,401 | 1/1989 | Kemp et al. | 514/255 |
| 4,804,662 | 2/1989 | Nickisch et al. | 514/252 |
| 4,806,536 | 2/1989 | Cross et al. | 514/252 |
| 4,806,555 | 2/1989 | Lunsford | 514/652 |
| 4,810,792 | 3/1989 | Kosley, Jr. | 546/207 |
| 4,845,099 | 7/1989 | Ruger et al. | 514/253 |
| 5,206,240 | 4/1993 | Baldwin | 514/231.5 |

FOREIGN PATENT DOCUMENTS

| 0121972 | 10/1984 | European Pat. Off. |
| 0235752 | 9/1987 | European Pat. Off. |
| 0285284 | 5/1988 | European Pat. Off. |
| 0285323 | 5/1988 | European Pat. Off. |
| 0281254 | 9/1988 | European Pat. Off. |
| 0284384 | 9/1988 | European Pat. Off. |
| 0286277 | 10/1988 | European Pat. Off. |
| 0286278 | 10/1988 | European Pat. Off. |
| 0300908 | 1/1989 | European Pat. Off. |
| 0307121 | 3/1989 | European Pat. Off. |
| 0397121 | 11/1990 | European Pat. Off. |
| 63-63533 | 12/1988 | Japan. |

OTHER PUBLICATIONS

J. Med. Chem., 19 1315 (1976) Bauer, et al.
II Farmaco-Ed Sci., 32 212–219 (1977) Lorio, et al.
J. Org. Chem. 41, No. 15 (1976) 2628–2633.

Primary Examiner—Celia Chang
Attorney, Agent, or Firm—Francis P. Bigley; Mark R. Daniel; Joseph F. DiPrima

[57] ABSTRACT

Spirocycles of the general structural formulae:

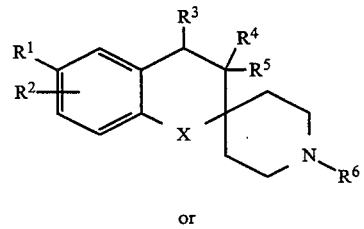

or

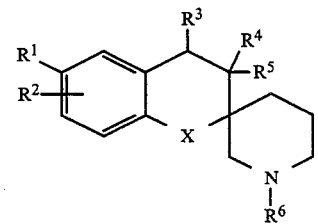

wherein:

X is O, $CH_2$ or $SO_m$;

$R^1$ is $AlkylSO_2NH-$, $AlkylO-$, $AlkylSO_2-$, $AlkylCONH-$, or $NO_2-$;

$R^2$ is $-H$, $-OAlkyl$, or $-Alkyl$;

$R^3$ is $-NHCOCH_2SO_mPhenyl$, $-NHCOCH_2SO_mAlkyl$, $-NHCOC(CH_3)_2OH$, or $NHSO_2Alkyl$;

$R^4$ and $R^5$ are $-H$, or $-Alkyl$;

$R^6$ is (Abstract continued on next page.)

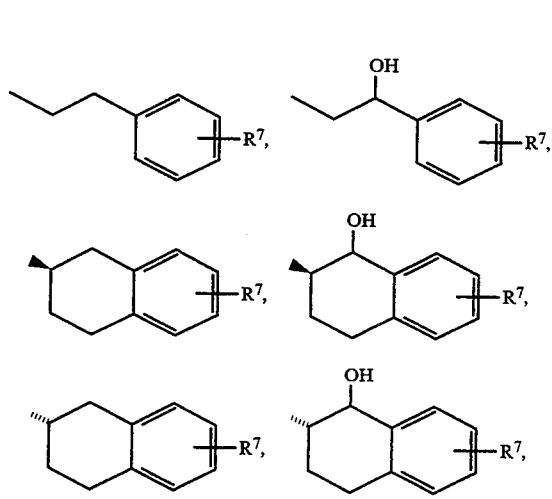
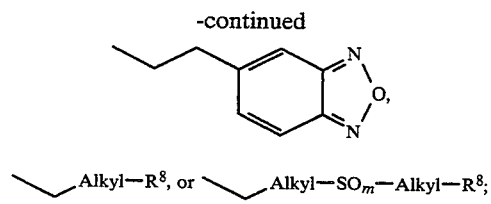
$R^7$ is —H, —CN, —NHSO₂Alkyl, —Br, —OAlkyl, —NH₂, —NO₂, —NHCOAlkyl, or NHCONHAlkyl;
$R_8$ is —H, —OH, —CN, —OAlkyl, —CONHAlkyl, —NHSO₂Alkyl, —NHCOAlkyl, —SO$_m$Alkyl, or —CO₂Alkyl;
and m is 0–2; or a pharmaceutically acceptable salt, hydrate or crystal form thereof; which are Class III antiarrhythmic agents.
13 Claims, No Drawings

SPIROCYCLES

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those having both satisfactory effects and high safety have not been obtained. For example, antiarrhythmic agents of Class I, according to the classification of Vaughan-Williams cause a selective inhibition of the maximum velocity of the upstroke of the action potential ($V_{max}$) and are inadequate for preventing ventricular fibrillation. In addition, they have problems regarding safety, namely, they cause a depression of the myocardial contractility and have a tendency to induce arrhythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs which cause a selective prolongation of the duration of the action potential without a significant depression of the $V_{max}$. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drags of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

A number of antiarrhythmic agents have been reported in the literature, such as those disclosed in:
(1) EP 397,121-A,
(2) EP 300,908-A,
(3) EP 307,121,
(4) U.S. Pat. No. 4,629,739,
(5) U.S. Pat. No. 4,544,654,
(6) U.S. Pat. No. 4,788,196,
(7) EP application 88302597.5,
(8) EP application 88302598.3,
(9) EP application 88302270.9,
(10) EP application 88302600.7,
(11 ) EP application 88302599.1,
(12) EP application 88300962.3,
(13) EP application 235,752,
(14) DE 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536.

Compounds of similar structure are found in Japanese patent publication 88-63533-B of Daiichi Pharmaceutical Co.; *J. Med. Chem.*, 19, 1315 (1976) by Bauer et al; Iorio et al in *Il. Farmaco-Ed Sci.*, 32, 212–219 (1977): Houlihan et al, U.S. Pat. No. 3,686,186; Davis et al, U.S. Pat. No. 4,420,485; Kealey, U.S. Pat. No. 4,810,792; Parham et al, *J. Org. Chem.*, 41, 2629 (1976). None of the compounds disclosed in the foregoing references are alleged to have antiarrhythmic activity.

Now with the present invention, there is provided as antiarrhythmic agents novel compounds with an increased degree of activity.

SUMMARY OF THE INVENTION

This invention is concerned with novel spirocycles of general structural formulae:

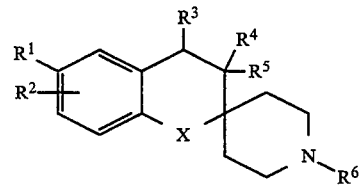

or

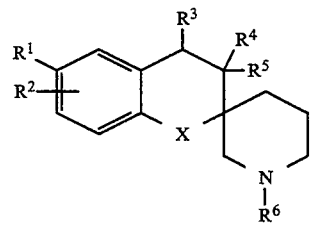

wherein:
X is O, $CH_2$ or $SO_m$;
$R^1$ is $AlkylSO_2NH-$, $AlkylO-$, $AlkylSO_2-$, $AlkylCONH-$, or $NO_2-$;
$R^2$ is $-H$, $-OAlkyl$, or $-Alkyl$;
$R^3$ is $-NHCOCH_2SO_m$Phenyl, $-NHCOCH_2SO_mAlkyl$,
$-NHCOC(CH_3)_2OH$, or $NHSO_2Alkyl$;
$R_4$ and $R_5$ are $-H$, or $-Alkyl$;
$R_6$ is

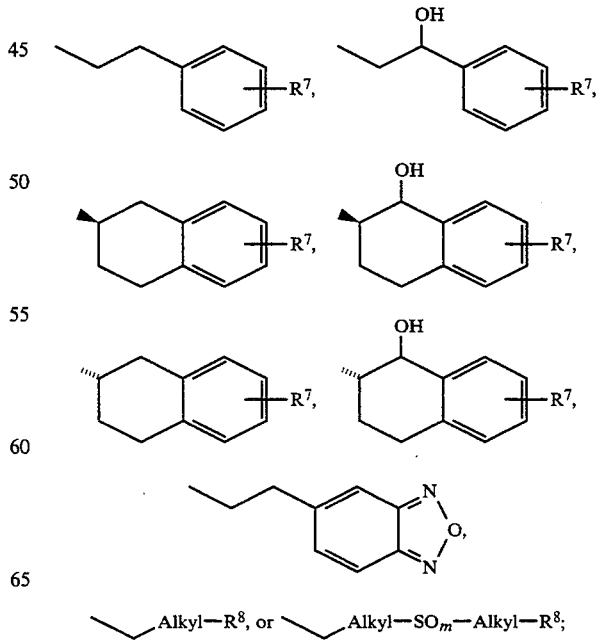

$R^7$ is —H, —CN, —NHSO$_2$Alkyl, —Br, —OAlkyl, —NH$_2$, —NO$_2$, —NHCOAlkyl, or NHCONHAlkyl;

$R^8$ is —H, —OH, —CN, —OAlkyl, —CONHAlkyl, —NHSO$_2$Alkyl, —NHCOAlkyl, —SO$_m$Alkyl, or —CO$_2$Alkyl;

and m is 0–2; or a pharmaceutically acceptable salt, hydrate or crystal form thereof.

The compounds of this invention are Class III antiarrhythmic agents and positive inotropic or cardiotonic agents.

The invention is also concerned with pharmaceutical formulations comprising one or more of the novel compounds as active ingredient, either alone or in combination with one or more of a Class I, Class II or Class IV antiarrhythmic agent, or a vasodilator, angiotensin convening enzyme inhibitor, angiotensin II antagonist, diuretic or digitalis.

The invention is also concerned with a method of treating arrhythmia and impaired cardiac pump functions with the above described novel compounds and formulations thereof.

The invention is also concerned with a method of treating arrhythmia and impaired cardiac pump functions with the above described novel compounds and formulations thereof in conjunction with a defibrillator.

The invention is further concerned with processes for preparing the novel compounds.

DETAILED DESCRIPTION OF THE INVENTION

The novel compound of this invention has structural formulae:

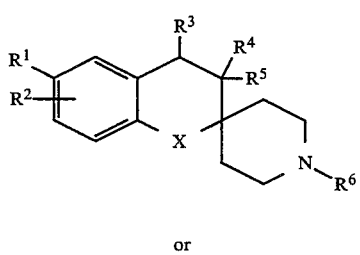

or

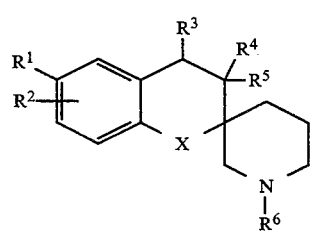

wherein:

X is O, CH$_2$ or SO$_m$;

$R^1$ is AlkylSO$_2$NH—, AlkylO—, AlkylSO$_2$—, AlkylCONH—, or NO$_2$—;

$R^2$ is —H, —OAlkyl, or —Alkyl;

$R^3$ is —NHCOCH$_2$SO$_m$Phenyl, —NHCOCH$_2$SO$_m$Alkyl, —NHCOC(CH$_3$)$_2$OH, or NHSO$_2$Alkyl;

$R^4$ and $R^5$ are —H, or —Alkyl;

$R^6$ is

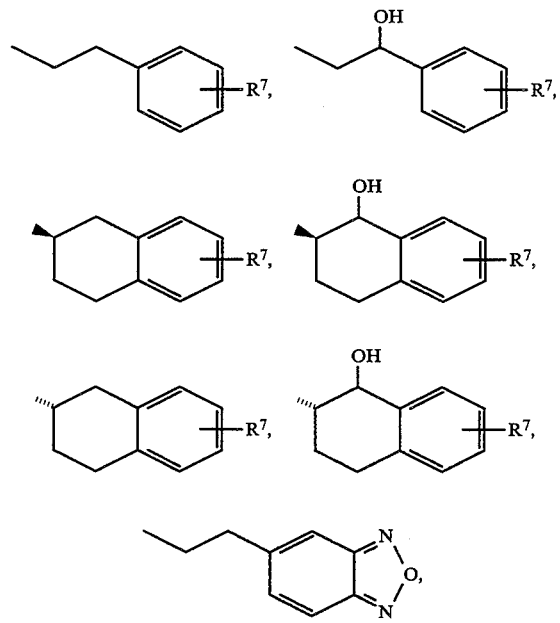

$R^7$ is —H, —CN, —NHSO$_2$Alkyl, —Br, —OAlkyl, —NH$_2$, —NO$_2$, —NHCOAlkyl, or NHCONHAlkyl;

$R^8$ is —H, —OH, —CN, —OAlkyl, —CONHAlkyl, —NHSO$_2$Alkyl, —NHCOAlkyl, —SO$_m$Alkyl, or —CO$_2$Alkyl;

and m is 0–2; or a pharmaceutically acceptable salt, hydrate or crystal form thereof.

In a preferred embodiment of the novel compound, X is O;

$R^1$ is H$_3$CSO$_2$NH—;

$R^2$ is —H;

$R^3$ is —NHCOCH$_2$SO$_m$Phenyl, —NHCOCH$_2$SO$_m$Alkyl, —NHCOC(CH$_3$)$_2$OH, or NHSO$_2$Alkyl;

$R^4$ and $R^5$ are —H;

and $R^6$ is

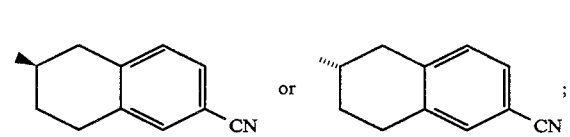

or a pharmaceutically acceptable salt, hydrate or crystal form thereof. Preferred compounds include:

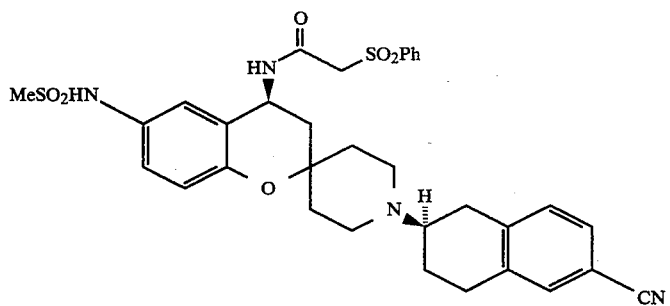

(4S, 2″R)-[(6-Cyano-1,2,3,4-tetrahydronaphthalene)-2-yl]-3,4-dihydro-6-methanesulfonamido-4-[2(phenylsulfonyl)acetamido]spiro(2H-1-benzopyran-2,4′-piperidine);

(4S, 2″R)-1′-[(6-Cyano-1,2,3,4-tetrahydronaphthalene)-2-yl]-3,4-dihydro-6-methanesulfonamido-4-[2-(phenylthio)acetamido]spiro(2H-1-benzopyran-2,4′-piperidine);

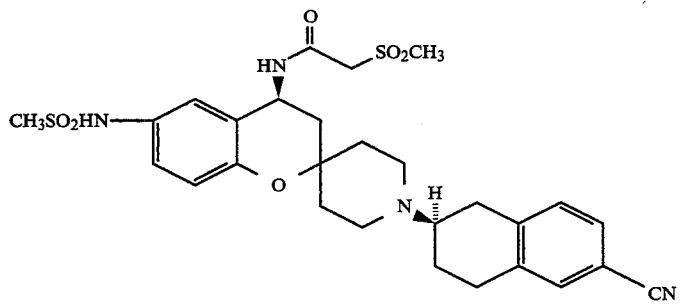

(4S, 2R)-1′-[(6-Cyano-1,2,3,4-tetrahydronaphthalene)-2-yl]-3,4-dihydro-6-methanesulfonamdo-4-[2-(methanesulfonyl)acetamido]spiro(2H-1-benzopyran-2,4′-piperidine);

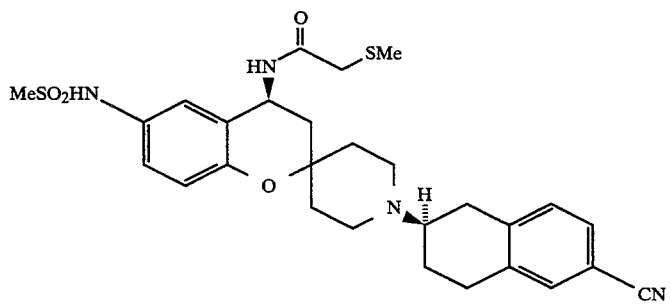

(4S, 2″R)-1′-[(6-Cyano-1,2,3,4-tetrahydronaphthalene)-2-yl]-3,4-dihydro-6-methanesulfonamido-4-[2-(methylthio)acetamido]spiro(2H-1-benzopyran-2,4′-piperidine);

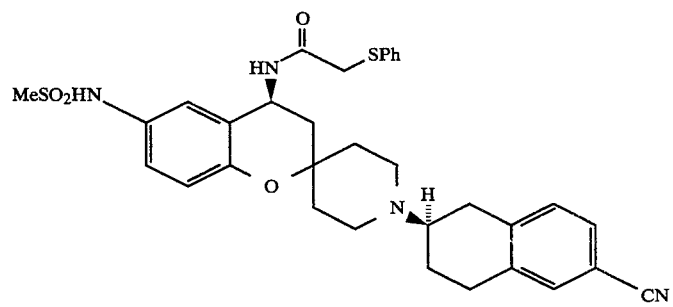

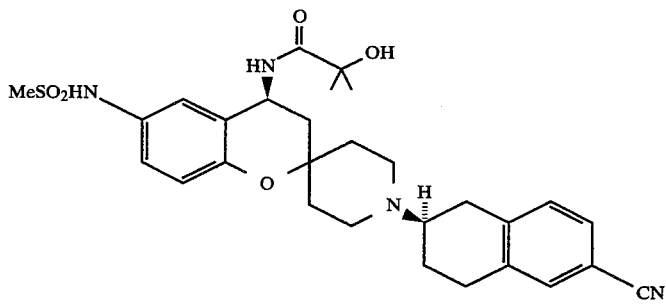

(4S, 2″R)-1′-[(6-Cyano-1,2,3,4-tetrahydronaphthalene)-2-yl]-3,4-dihydro-4-[(2-hydroxy-2-methyl)-propanamido]-6-methanesulfonamidospiro(2H-1-benzopyran-2,4′-piperidine);

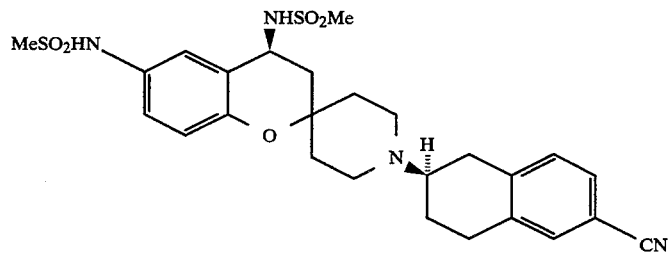

(4S, 2″R)-1′-[(6-Cyano-1,2,3,4-tetrahydronaphthalene)-2-yl]-3,4-dihydro-4,6-bis(methanesulfonamido)spiro(2H-1-benzopyran-2,4′-piperidine);
or pharmaceutically acceptable salts, hydrates and crystal forms thereof.

The term "Alkyl", if the number of carbons is unspecified, means $C_1$–$C_8$ alkyl, and "Alkyl" of three or more carbon atoms includes straight, branched and cyclic chains.

Also included within the scope of the present invention are the non-toxic pharmaceutically acceptable salts of the novel compounds. Acid addition salts are formed by mixing a solution of the compound with a solution of a pharmaceutically acceptable non-toxic acid such as hydrochloric acid, fumaric acid, maleic acid, methanesulfonic acid, isethionic acid, succinic acid, acetic acid, citric acid, tartaric acid, phosphoric acid, or the like. Also included within the scope of this invention are N-oxides.

Also included within the scope of this invention are diastereomers and enantiomers of the novel compounds and mixtures thereof.

The novel compounds of the present invention, have the pharmacological properties required for the antiarrhythmic agents of Class III, namely the prolongation of the myocardial action potential in vitro, without a significant depression of the $V_{max}$, and the prolongation of $QT_c$-interval in anesthetized dogs.

In addition, these compounds also have the pharmacological properties required for the antiarrhythmic agents of Class III. Moreover, the members of both groups of compounds in general are much more potent than the reference drug, sotalol.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds, or a pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrate. Examples of angiotensin converting enzyme inhibitors include enalapril, lisinopril and captopril. Examples of diuretics include hydrochlorothiazide and acetazolamide. Exemplary of an angiotensin II antagonist is losartan. The pharmaceutical agents listed herein are examples and do not represent a complete listing of the many compounds in these classes which are contemplated by this invention.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, controlled release delivery systems or the like prepared by art recognized procedures. The amount of active compound in such therapeutically useful compositions or preparations is such that a suitable dosage will be obtained.

EXAMPLES

The following examples are given for the purpose of illustrating the present invention and shall not be construed as being limitations on the scope or spirit of the instant invention.

The novel processes of this invention can be exemplified by the following Reaction Schemes:

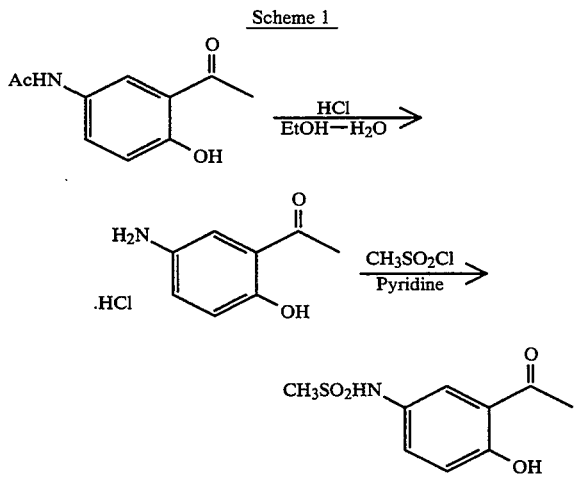

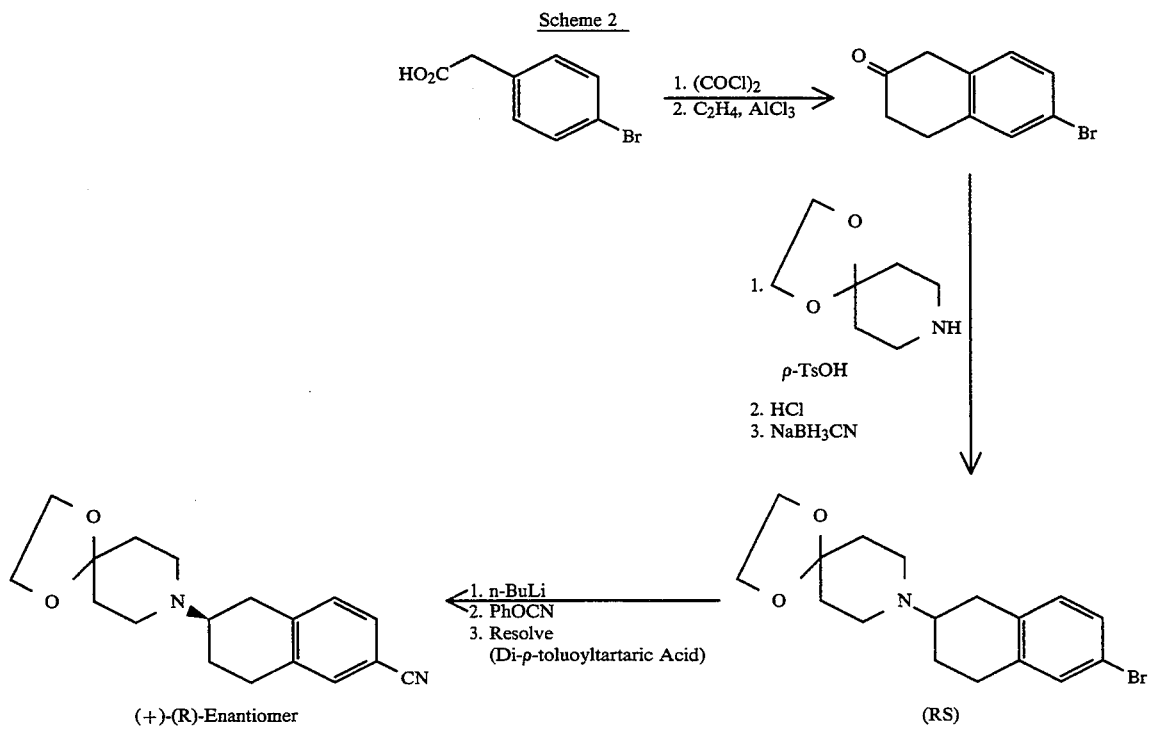

Scheme 3
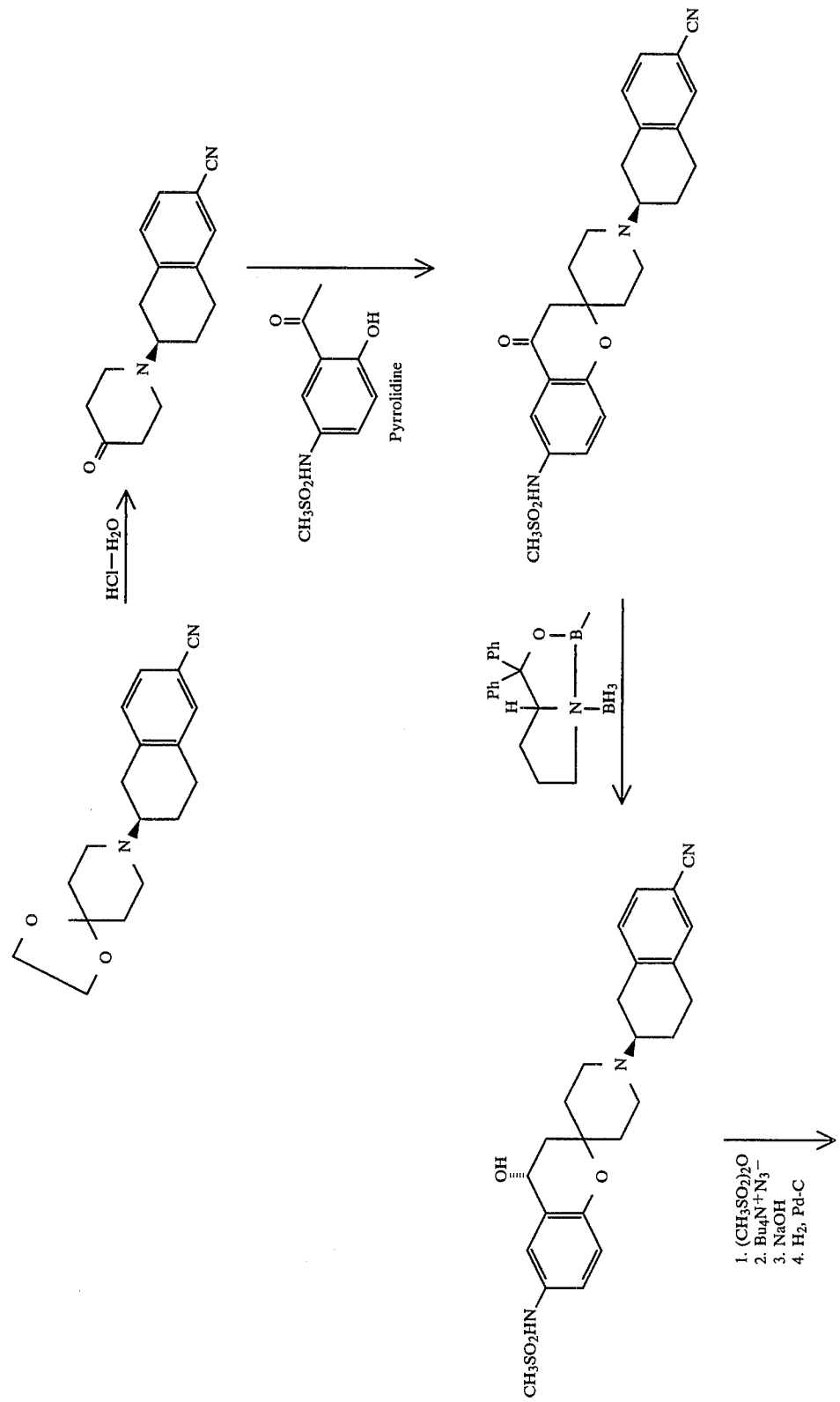

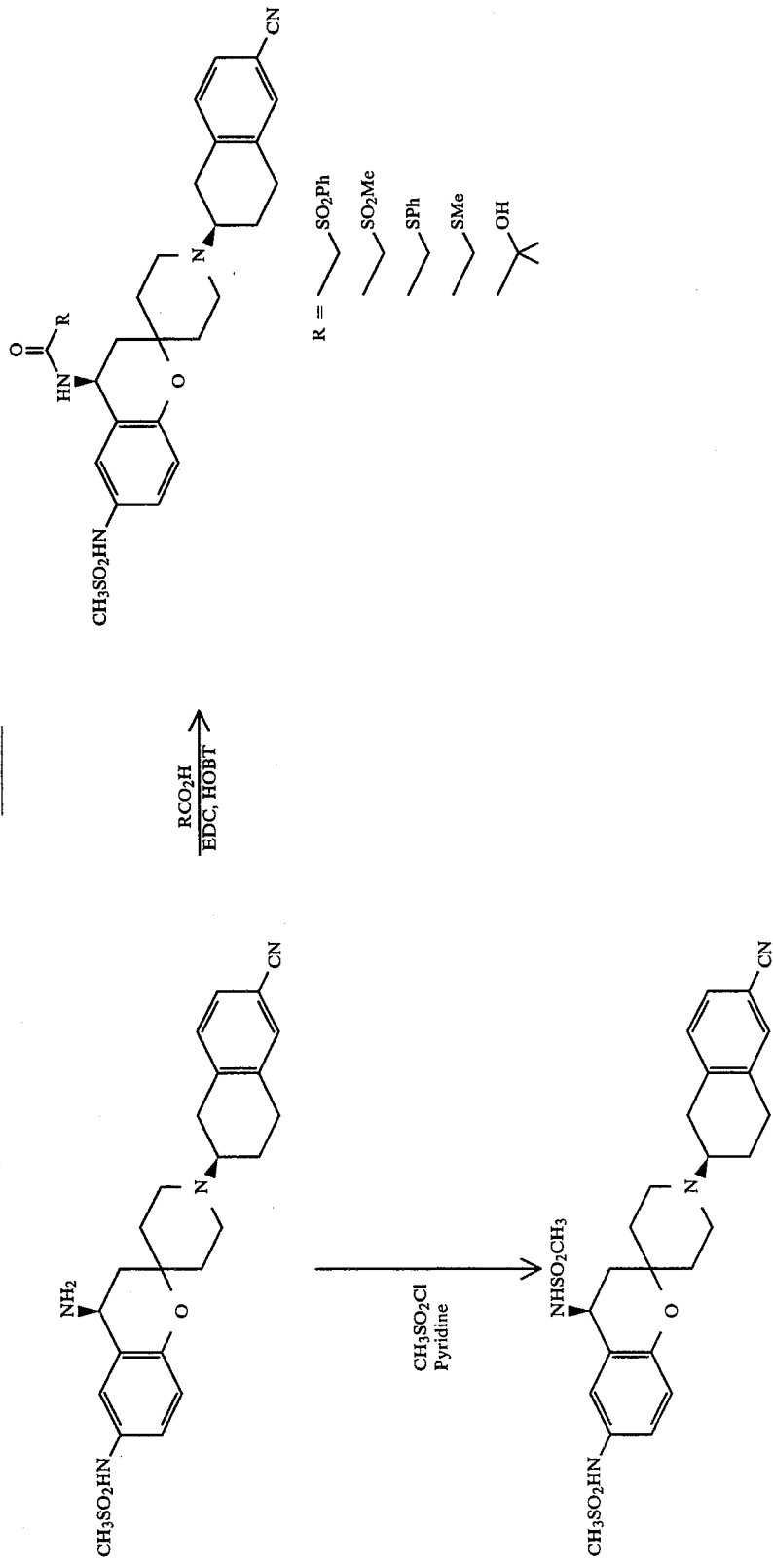

SCHEME 1

5-Amino-2-hydroxyacetophenone hydrochloride

5-Acetamido-2-hydroxyacetophenone (19.03 g, 98.5 mmol) [prepared as described by C. T. Chang, F. C. Chen, K. K. Hsu, T. Ueng, and M. Hung, *J. Chem. Soc.* 3414 (1961)] dissolved in 300 mL of ethanol and 100 mL of 6N aqueous HCl was heated at reflux for 8 h. The solution was concentrated in vacuo, and the residue was flushed with ethanol, and dried in vacuo to give 5-amino-2-hydroxyacetophenone hydrochloride as a dark solid (18.3 g, 99%).

N-(3-Acetyl-4-hydroxyphenyl)methanesulfonamide

A suspension of 5-amino-2-hydroxyacetophenone hydrochloride (18.39 g, 98 mmol) in methylene chloride (200 mL) cooled to 0° C. was treated with pyridine (19.4 mL, 240 mmol). Methanesulfonyl chloride (7.74 mL, 100 mmol) was added dropwise. The mixture was stirred an additional 30 min. at 0° C. and then allowed to warm to room temperature over 1 h. The mixture was diluted with methylene chloride (200 mL) and washed with 1N aqueous HCl (50 mL). Concentration of the organic layer and trituration with methylene chloride gave a solid which was recrystallized from methylene chloride to give of N-(3-acetyl-4-hydroxyphenyl)methanesulfonamide as a white solid-(15.45 g, 69%), m.p. 121–122° C.

SCHEME 2

6-Bromo-3,4-dihydro-2(1H)-napthalenone

A single neck 3 liter round bottom flask under an Ar atmosphere was charged with 4-bromobenzeneacetic acid (250.0 g, 1.15 mol), methylene chloride (1.5 L) and dimethylformamide (0.5 mL). This magnetically stirred solution was cooled to 0° C. and treated dropwise with oxalyl chloride (156 mL, 1.74 mol). The reaction was allowed to reach room temperature and stirred 16 h. The reaction was concentrated on a rotary evaporator to approximately 1 L of volume. A separate dry 5 liter 3 neck round bottom flask under Ar, fitted with gas inlet tube, overhead stirrer, and digital thermometer was charged with methylene chloride (1.5 L) and AlCl$_3$ (312.0 g, 2.34 mol). This suspension was cooled to 0° C. and stirred while the above solution of acid chloride was added to it slowly via cannula. When the addition was complete, ethylene gas was introduced for 1–2 h. to the vigorously stirred suspension while maintaining the internal temperature at 15° C. Upon completion by HPLC, the reaction was warmed to room temperature and stirred for 0.5 h. The mixture was recooled to 0° C. and cautiously quenched slowly with water (1.5 L). The layers were separated, and the aqueous one washed with methylene chloride (500 mL). The organic portion was washed with 2N aqueous HCl (2×800 mL), brine (400 mL), and saturated aqueous NaHCO$_3$ (2×800 mL). Each aqueous extract was washed with the same 500 mL methylene chloride extract from above. The methylene chloride extracts were combined, dried (Na$_2$SO$_4$), filtered, and concentrated to approximately 500 mL of volume. This was then added to 5.0 L of hexane warmed to 50° C. The methylene chloride was distilled off and the hot solution decanted from an insoluble brown tar. The solution was allowed to cool to 25° C. and placed in the freezer overnight. The precipitate was collected and washed with hexane (200 mL), and dried in vacuo to give 229.0 g of 6-bromo-3,4-dihydro-2(1H)-napthalenone as a pale yellow solid (88%).

(2RS)-1,4-Dioxa-8-(6-bromo-1,2,3,4-tetrahydronaphth-2-yl)-8-azaspiro[4.5]decane A 3 L round bottom flask fitted with an argon inlet, and Deak-Stark apparatus was charged with a solution of 6-bromo-3,4-dihydro-2(1H)napthalenone (100.0 g, 445 mmol) in toluene (2.0 L). Para-toluenesulfonic acid (0.50 g) and 1,4-dioxa-8-azaspiro[4,5]decane (81.5 g, 489 mmol) were added and the stirred mixture heated to reflux and the water removed (4.5 h.). The mixture was cooled, and concentrated to an oil in vacuo. The oil was dissolved in anhydrous tetrahydrofuran (1.5 L) and cooled to 0° C. under argon. Dry HCl gas was introduced (at below 5° C.) and a solid precipitate formed. Sodium cyanoborohydride (36.3 g, 578 mmol) was added in four portions. The reaction was allowed to warm gradually to room temperature and stirred 16 h. This was quenched with 1N aqueous sodium hydroxide (500 mL) and stirred for 0.5 h. (pH=13.5). The mixture was concentrated on a rotary evaporator to remove THF, and diluted with 1N aqueous sodium hydroxide (1.1 L) and diethyl ether (1.5 L). This mixture was stirred 15 min., the layers were separated and the aqueous layer was washed with diethyl ether (2×200 mL). The organic layers were combined, washed with water (2×500 mL) and saturated aqueous NaCl (2×250 mL) and then with 1N aqueous HCl (1×1.0 L, 2×500 mL). The acid extracts were combined, stirred with methylene chloride (1.0 L), and basified with 40% aq. NaOH (pH=10). The layers were separated, and the aqueous extracted with methylene chloride (500 mL). The methylene chloride extracts were combined, dried (Na$_2$SO$_4$), and concentrated to an oil. The oil was flushed with toluene (2×400 mL) and dried in vacuo to give (2RS)-1,4-dioxa-8-(6-bromo-1,2,3,4-tetrahydronaphth-2-yl)-8-azaspiro[4.5]decane as a solid on standing (128.8 g, 87%) which was greater than 98% pure by HPLC and used in the next step without purification. Note: The amount of excess HCl gas present (pH=3–4, THF suspension on wet pH paper) critically determines the yield of free amine. Additional HCl may be added during the introduction of the cyanoborohydride. In runs in which the pH was not adjusted properly the yield was reduced to 50%; the balance being a borane complex which was isolated from the ether layers. This borane complex could be quantitatively convened to the free amine by heating in 40% aqueous NaOH/ethylene glycol (1:1) at 100° C.

Phenyl cyanate

The title compound was prepared by a modification of the procedure described in *Organic Syntheses*, 61, 35 (1983). A 3-necked, 2 L R.B. flask, equipped with a 500 mL pressure equalized dropping funnel, a mechanical stirrer and a thermometer, was charged with water and cooled in an ice-salt bath. Cyanogen bromide (189.1 g, 1.78 mol) was added and the mixture was stirred for 5 min. Phenol (160.0 g., 1.7 mol) in carbon tetrachloride (535 mL) was added in one portion. The mixture was stirred vigorously while triethylamine (236.9 mL, 172.0 g, 1.7 mol) was added dropwise at a rate such that the reaction temperature did not exceed 5° C. (total addition time=45 min.). The mixture was stirred for a further 15 min. then transferred to a 2 L separatory funnel. The organic layer was separated and the aqueous layer was extracted with carbon tetrachloride (2×90 mL).

The combined organic layers were washed with water (3×90 mL) then dried by stirring with phosphorus pentoxide (10 g) for 15 min. The mixture was filtered and the solvent was evaporated under reduced pressure (water aspirator) at 20° C. to give a yellow oil. Polyphosphate ester [Y. Kanaoka, et al., Chem. Pharm. Bull., 13, 1065–1072 (1965)](0.2 mL) was added and the mixture was distilled under reduced pressure through a 15 cm Vigreux column to give phenyl cyanate (165.8 g, 82%) as a colorless oil, b.p. 79–82° C. (16 mmHg). The product was stored under nitrogen at −10° C. (freezes).

δSH(CDCl$_3$) 7.49–7.30 (5H, m).

(2RS)-1,4-Dioxa-8-(6-cyano-1,2,3,4-tetrahydronaphth-2-yl)-8-azaspiro[4.5]decane (2RS)-1,4-Dioxa-8-(6-bromo-1,2,3,4-tetrahydronaphth-2-yl)-8-azaspiro[4.5]decane (70.4 g, 0.2 mol) under nitrogen in a 1 L R.B. flask was dissolved in anhydrous THF (600 mL, distilled from Na/benzophenone) and cooled to −75° C. Phenyl cyanate (26.06 mL, 28.5 g, 0.24 mol) dissolved in anhydrous THF (400 mL) under nitrogen in a 2 L R.B. flask equipped with a digital thermometer was cooled to −75° C. n-Butyl lithium (1.6M in hexane, 137.5 mL, 0.22 mmol) was added over 5 min. to the bromide solution. Further n-butyl lithium (1.6M in hexane, 12.5 mL, 0.02 mmol) was added to the phenyl cyanate solution. After 5 min., the lithinted bromide solution was added over 5 min., via cannula, to the phenyl cyanate solution (reaction temperature rises to −35° C.). The mixture was stirred and cooled to −75° C. for 30 min. then the cooling bath was removed and HCl-H$_2$O (1M, 200 mL) was added with vigorous stirring. The mixture was warmed to room temperature, diluted with HCl-H$_2$O (1M, 1800 mL) and washed with ether (2×1000 mL.). Methylene chloride (1000 mL) was added and the mixture was stirred and cooled in ice during the addition of aqueous sodium hydroxide 10M, 180 mL). The layers were separated, and the aqueous layer was extracted with methylene chloride (500 mL). The combined organic layers were dried (Na$_2$SO$_4$), and the solvent was evaporated under reduced pressure to give crude (2RS)-1,4-dioxa-8-(6-cyano-1,2,3,4-tetrahydronaphth-2-yl)-8-azaspiro[4.5]decane as a tan solid (56.2 g). Crude (2RS)-1,4-dioxa-8-(6-cyano-1,2,3,4-tetrahydronaphth-2-yl)-8-azaspiro[4.5]decane in three batches (56.4 g, 56.2 g, 27.7 g; total 140.3 g) were separately dissolved in refluxing methylcyclohexane (1000 mL each) and combined by decanting into a 5 L, 4-necked flask equipped with a mechanical stirrer, thermometer, reflux condenser and a stopper. The mixture was heated to reflux (clear solution formed), then allowed to cool with stirring to room temperature, then to 5° C. The mixture was stored at −15° C. for 15 h. The solid was collected by filtration, washed with cold methylcyclohexane (2×150 mL) and dried in vacuo at room temperature to give (2RS)-1,4-dioxa-8-(6-cyano-1,2,3,4-tetrahydronaphth-2-yl)-8-azaspiro[4.5]decane as a pale yellow solid (121.3 g), m.p. 136–138° C.

Resolution of 1,4-dioxa-8-(6-cyano-1,2,3,4-tetrahydronaphth-2-yl)-8-azaspiro[4.5]decane To a solution of 5.00 g (0.0168 mol) of racemic 1-4-dioxa-8-(6-cyano-1,2,3,4-tetrahydronaphth-2-yl)-8-azaspiro[4.5]decane in 500 mL of boiling absolute ethanol was added 6.47 g (0.01676 mol) of di-p-toluoyl-D-tartaric acid. The solution was concentrated by boiling to 450 mL and allowed to stand overnight at room temperature. The product that crystallized was removed by filtration and was washed with ethanol to give 4.45 g of a salt, A. The tiltrate and washings were combined and evaporated to give B. The solid A was recrystallized three times from absolute ethanol to yield 2.82 g of salt having $[\alpha]_{589}$=+106.1° (c=1.151; pyridine). This salt was converted to the free base using sodium bicarbonate solution and extracting into ethyl acetate. The ethyl acetate phase was dried over magnesium sulfate, filtered, and concentrated in vacuo to give (+)-(2R)-1,4-dioxa-8-(6-cyano-1,2,3,4-tetrahydronaphth-2-yl)-8-azaspiro[4.5]decane (1.15 g), m.p. =124–126 ° C., $[\alpha]_{589}$=+55.4° (c=1.605; CHCl$_3$).

The solid B was converted to the free base as described above to give 2.84 g of material. This solid (0.00938 mol) was dissolved in 275 mL of boiling ethanol and was treated with 3.794 g (0.00938 mol) of di-p-toluoyl-L-tartaric acid monohydrate. The salt that crystallized on cooling was collected by filtration and was washed with ethanol to give 4.47 g of material having $[\alpha]_{589}$=−102.6° (c=1.131; pyridine). Recrystallization of this material from ethanol gave 3.71 g of salt, $[\alpha]_{589}$=−106.1° (c=0.985, pyridine), and further recrystallization from ethanol gave 3.24 g of salt having essentially no change in rotation, $[\alpha]_{589}$=−105.9° (c=1.472, pyridine). This salt was converted to the free base as described above to give (−)-(2S)-1,4-dioxa-8-(6-cyano-1,2,3,4-tetrahydronaphth-2-yl)-8-azaspiro[4.5]decane (1.34 g), m.p.=124–126° C., $[\alpha]_{589}$=−54.5° (c=1.954; CHCl$_3$).

SCHEME 3

(2RS)—, (+)-(2R)—, and (−)-(2S)-1-(6-Cyano-1,2,3,4-tetrahydronaphth-2-yl)-4-piperidinone A solution of 1,4-dioxa-8-(6-cyano-1,2,3,4-tetrahydronaphth-2-yl)-8-azaspiro[4.5]decane hydrochloride (10.0 g, 30.0 mmol) or the resolved free base was dissolved in 1N aqueous HCl (100 mL). This was stirred and heated to 100° C. under an argon atmosphere for 1.5 h. The solution was cooled in an ice bath to 25° C. and methylene chloride added (200 mL). The mixture was stirred and basified to pH 9.0 with saturated aqueous sodium carbonate. The organic layer was separated and the aqueous layer was extracted with methylene chloride (2×50 mL). The combined organic extract was dried (Na$_2$SO$_4$), and concentrated to give 1-(6-cyano-1,2,3,4-tetrahydronaphth-2-yl)-4-piperidinone as a foam (7.5 g, 99%), 98% by HPLC [HPLC conditions, column: Waters C18 μBondapak, eluent: 0.1% H$_3$PO$_4$ in H$_2$O: CH$_3$CN (85:15), flow: 2 mL/min., wavelength: 220 nm, R$_t$: ketal=6.20 min., ketone=2.1 min.].

(2″RS)—, (+)-(2″R)—, and (−)-(2″S)-1′-[(6-Cyano-1,2,3,4-tetrahydronaphthalene)-2-yl]-3,4-dihydro-6-methanesulfonamidospiro(2H-1-benzopyran-2,4′-piperidine)-4-one hydrochloride A solution of N-(3-acetyl-4-hydroxyphenyl)methanesulfonamide (5.58 g, 24.3 mmol), and pyrrolidine (2.05 mL, 24.3 mmol) in methanol (30 mL) was stirred at 60° C. for 10 min. (2RS)-1-(6-cyano-1,2,3,4-tetrahydronaphth-2-yl)-4-piperidinone (3.09 g, 12.2 mmol) was added in one portion and the mixture stirred for 1.5 h. at 60° C. The reaction was concentrated to an oil in vacuo and flash chromatographed (silica gel, ethyl acetate) to afford the product in appropriate fractions which were combined and concentrated to 350 mL and treated with 1.3N HCl in isopropyl alcohol. The precipitate was stirred 2 h., filtered, and dried in vacuo (60° C., 0.1 torr) to give (2"RS)-1'-[(6-cyano-1,2,3,4-tetrahydronaphthalene)-2-yl]-3,4-dihydro-6-methanesulfonamidospiro(2H-1-benzopyrano2,4'-piperidine)-4-one hydrochloride, (3.91 g, 64%), m.p. 250–252° C.

In the same way, starting from (+)-(2R)-1-(6-cyano-1,2,3,4-tetrahydronaphth-2-yl)-4-piperidinone, (+)-(2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-one hydrochloride was obtained, m.p.=262–264 ° C. (dec), $[\alpha]_d = +40.7°$ (c=0.17 MeOH).

In the same way, starting from (−)-(2S)-1-(6-cyano-1,2,3,4-tetrahydronaphthalene)-2-yl)-4-piperidinone, (−)-(2"S)-1'-[(6-cyano-1,2,3,4-tetrahydronaphthalene)-2-yl]-3,4-dihydro-6-methanesulfonamidospiro(2H-1-benzopyran-2,4'-piperidine)-4-one hydrochloride was obtained, m.p.=263–265° C. (dec), $[\alpha]_d = -41.36°$ (c=0.191 MeOH).

(+)-(4R, 2"R)-1'-[(6-Cyano-1,2,3,4-tetrahydronaphthalene)-2-yl]-3,4-dihydro-6-methanesulfonamidospiro(2H-1-benzopyran-2,4'-piperidine)-4-ol hydrochloride An oven dried 1000 mL single necked R.B. flask equipped with a magnetic stirrer bar, septum cap and thermocouple temperature probe was charged with (+)-(2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-one [contains 6.3 % $CH_2Cl_2$ by weight (determined by $^1H$ N.M.R.), 11.33 g, 22.81 mmol]. Methylene chloride (456 mL) was added and the mixture was stirred under argon until a clear yellow solution had formed (10 min.). The flask was cooled in a dry ice/isopropanol bath to give an internal temperature of −20° C. An oven dried 200 mL single necked R.B. flask equipped with a magnetic stirrer bar and septum cap was charged with (S)-tetrahydro-1-methyl-3,3-diphenyl-1H,3H-pyrrolo[1,2,c][1,3,2]oxazaboroleborane complex (*J. Org. Chem.* 1993, 58, 2880–2888) (7.96 g, 27.37 mmol), methylene chloride (114 mL) was added and the mixture was stirred under argon until a clear colorless solution had formed (2 min.). The oxazaboroleborane solution was added dropwise via syringe over 15 min. to the ketone solution (reaction temperature rises to −15° C.). The reaction was stirred under argon for 1 h., maintaining the internal temperature at −15° C., then the cooling bath was removed and the mixture was stirred for 1 h., warming slowly to room temperature. Methanol (30 mL) was added dropwise over 2 min. and the solvent was evaporated under reduced pressure to give an off white foam. Methanol (750 mL) was added and the volume was reduced by distillation (1 Atm.) to 250 mL. Further methanol (500 mL) was added and the volume was reduced by distillation (1 Atm.) to 250 mL. The remaining solvent was evaporated under reduced pressure to give a yellow foam. The flask was equipped with a magnetic stirrer bar, septum cap and thermocouple temperature probe and methylene chloride (456 mL) was added. The mixture was cooled in an ice-water bath to an internal temperature of 0° C. and acetic anhydride (2.71 mL, 2.93 g, 28.74 mmol) was added dropwise via syringe over 2 min. The mixture was stirred at 0° to 5° C. for 1 h, further acetic anhydride (0.137 mL, 0.14 g, 1.37 mmol) was added via syringe in one portion and the mixture was stirred at 0° to 5° C. for 1 h. Methanol (100 mL) was added and the cooling bath was removed. The mixture was stirred at room temperature for 18 h. and poured into a mixture of aqueous sodium hydrogen carbonate (saturated, 400 mL) and water (100 mL) in a 2 L separatory funnel. The layers were separated and the aqueous layer was extracted with methylene chloride (2×200 mL). The organic fractions were combined and dried by stirring over $Na_2SO_4$ (anhydrous, 20 g) for 10 min. The drying agent was removed by filtration through a glass sinter (medium porosity) and the solvent was evaporated under reduced pressure to give an off-white foam. A silica flash chromatography column (7 cm dia., 20 cm length) was prepared by dry packing and eluting with $CH_2Cl_2/MeOH/NH_3-H_2O$ (93:7:0.7, 3000 mL, 5 p.s.i.). The crude product was dissolved in methylene chloride and purified on the flash column, eluting with the above solvent mixture. Fractions containing the alcohol were combined, evaporated under reduced pressure, redissolved in $CH_2Cl_2$ (50 mL), filtered through a short column of anhydrous $Na_2SO_4$ (2.5 cm dia., 6 cm length) washing with further methylene chloride and evaporated under reduced pressure to give an off-white foam (11.63 g). Ethanol (114 mL) was added and the mixture was stirred until a clear solution had formed (2 min.). Water (114 mL) was added and the mixture was heated to reflux (clear solution forms). The mixture was allowed to cool to room temperature then stored at −15° C. for 18 h. The solid was collected by filtration and dried in vacuo over $P_2O_5$ at room temperature for 8 h., then at 30° C. for 15 h to give a white solid (9.73 g). The solid was placed in a 200 mL single necked R.B. flask equipped with a magnetic stirrer bar, septum cap and thermocouple temperature probe, ethanol (100 mL) was added, the flask was cooled in a water bath to 15° C. and the mixture was stirred under argon until a clear solution had formed (10 min.). An ethanolic solution of hydrogen chloride (3.2 M, 6.35 mL, 20.31 mmol) was added over 45 min. via syringe with vigorous stirring (internal temperature rises to 20° C.) and the mixture was stirred at room temperature for 3 h., then cooled to −15° C. for 20 h. The solid was collected by filtration under argon and dried in vacuo at room temperature for 2 days, then at 35° C. for 24 h to give a white solid (10.33 g). A portion of the solid (10.10 g) was placed in a 1000 mL conical flask equipped with a magnetic stirrer bar and thermocouple temperature probe. Ethanol (100 mL) and water (100 mL) were added and the mixture was stirred to give a clear solution (10 min.). Further water (600 mL) was added and the mixture was heated in a water bath to 50° C. (internal temperature) to give a clear solution. The water bath was removed and the mixture was allowed to cool, with stirring, to room temperature, then in ice-water to 5° C. The thermocouple was removed and the flask was stoppered and stored at 0° C. for 16 h. The solid was collected by filtration and dried in vacuo over $P_2O_5$ at room temperature for 24 h., then at 35° C. for 48 h to give (+)-(4R, 2"R)-1'-[(6-cyano-1,2,3,4-tetrahydronaphthalene)-2-yl]-3,4-dihydro-6-methanesulfonamidospiro(2 H-1-benzopyran-2,4'-piperidine)-4-ol hydrochloride as a white solid (5.98 g, 52%), m.p. 202–204° C. (softens at 195° C.), $[\alpha]_d + 28.9°$ (c=0.194 g/100 mL, MeOH).

Elemental analysis for $C_{25}H_{30}ClN_3O_4S \cdot 0.65H_2O$:
Calculated; C 58.21; H 6.12; N 8.15%.
Found; C 58.23; H 6.05; N 8.19%.

(4S, 2″R)-1′-[(6-Cyano-1,2,3,4-tetrahydronaphthalene)-2-yl]-3,4-dihydro-6-methanesulfonamidospiro( 2H-1-benzopyran-2,4′-piperidine)-4-amine dihydrochloride (+)-(4R, 2″R)-1′-[(6-Cyano-1,2,3,4-tetrahydronaphthalene)-2-yl]-3,4-dihydro-6-methanesulfonamidospiro(2H- 1-benzopyran-2,4′-piperidine )-4-ol (3.60 g, 7.7 mmol) was dissolved in methylene chloride (120 mL) and cooled to −50° C. A solution of methanesulfonic anhydride (3.22 g, 18.5 mmol) in methylene chloride (35 mL) was added and the mixture was stirred at −45° C. A solution of diisopropylethylamine (2.75 mL, 2.04 g, 15.8 mmol) in methylene chloride (10 mL) was added slowly and the mixture was stirred at −20° C. for 15 min. A solution of tetrabutylammonium azide (8.32 g, 29.1 mmol) in methylene chloride (10 mL) was added slowly and the mixture was stirred at room temperature for 1 h. The mixture was filtered through silica gel washing with methylene chloride (500 mL) then with ethyl acetate (3000 mL). The ethyl acetate fractions were evaporated under reduced pressure to give a colorless foam (4.07 g). The residue was dissolved in methanol (200 mL), aqueous sodium hydroxide (1 M, 100 mL) and methylene chloride (50 mL) were added and the mixture was stirred at room temperature for 3 h. The methanol was evaporated under reduced pressure, water (100 mL) and methylene chloride (250 mL) were added and the pH was adjusted to 9.0 with hydrochloric acid (conc.) The layers were separated and the aqueous layer was extracted with methylene chloride (125 mL). The combined organic fractions were dried (Na$_2$SO$_4$) and evaporated under reduced pressure to give a colorless foam (3.70 g). The residue was dissolved in ethanol (300 mL), palladium on carbon (10%, 0.75 g) was added and the mixture was stirred under hydrogen (1 Atm.) for 16 h. The mixture was filtered through celite and the solvent was evaporated under reduced pressure to give a colorless foam (3.44 g). A sample (0.5 g) was purified by flash column chromatography on silica gel, eluting with CH$_2$Cl$_2$/MeOH/NH$_3$ (Aq.) (95:5:1) to give (4S, 2″R)-1′-[(6-cyano-1,2,3,4-tetrahydronaphthalene)-2-yl]-3,4-dihydro-6-methanesulfonamidospiro(2H-1-benzopyran-2,4′-piperidine)-4-amine (0.38 g, 73%). The residue was dissolved in ethyl acetate (20 mL) and HCl-$^i$PrOH (1.3M, 1.6 mL) was added dropwise with stirring. The mixture was stirred at ambient temperature for 1 h., hexane (50 mL) was added slowly and the mixture was stirred at ambient temperature for 1 h. The solid was collected and dried in vacuo at room temperature to give (4S, 2″R)-1′-[(6-cyano-1,2,3,4-tetrahydronaphthalene )-2-yl]-3,4-dihydro-6-methanesulfonamidospiro(2H- 1-benzopyran-2,4′-piperidine )-4-amine dihydrochloride as a colorless solid (0.403 g), m.p. 242–245° C. (dec.).

Elemental analysis for C$_{25}$H$_{30}$N$_4$O$_3$S.2HCl.H$_2$O
Calculated; C 53.85; H 6.15; N 10.05%.
Found; C 53.88; H 6.23; N 10.08%.

EXAMPLE 1

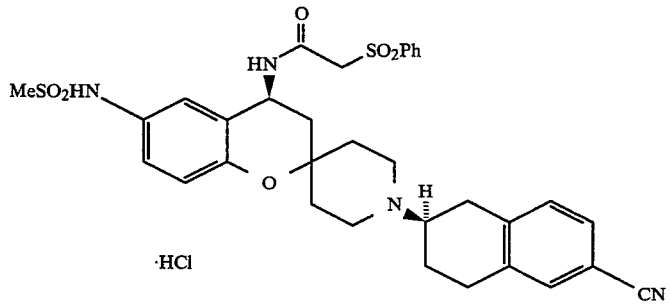

(−)-(4S, 2″R)-1′-[(6-Cyano-1,2,3,4-tetrahydronaphthalene)-2-yl]-3,4-dihydro-6-methanesulfonamido-4-[2-(phenylsulfonyl)acetamido]spiro(2H-1-benzopyran-2,4′-piperidine) hydrochloride 1-(3-Dimethylaminopropyl)-3-ethylcarbodiimide hydrochloride (86 mg, 0.44 mmol) was added to a stirred, cooled (0° C.) solution of (4S, 2″R)-1′-[ (6-cyano-1,2,3,4-tetrahydronaphthalene)-2-yl]-3,4-dihydro-6-methanesulfonamidospiro(2H-1-benzopyran-2,4′-piperidine)-4-amine (186 mg, 0.40 mmol), phenylsulfonylacetic acid (88 mg, 0.44 mmol), 1-hydroxybenzotriazole (67 mg, 0.44 mmol) and DMF (4 drops) in methylene chloride (2 mL). The mixture was stirred at room temperature for 18 h., poured into saturated aqueous sodium hydrogen carbonate (30 mL) and extracted with methylene chloride (4×50 mL). The combined organic fractions were dried (Na$_2$SO$_4$) and evaporated under reduced pressure. The residue was purified by flash column chromatography on silica gel, eluting with CH$_2$Cl$_2$/MeOH/NH$_3$ (Aq.) (98:2:0.2 increasing to 94:6:0.6) to give a colorless solid (86 mg, 32%). The residue was suspended in ethanol (10 mL) and HCl-EtOH (6M, 2 mL) was added dropwise with stirring. The mixture was stirred at ambient temperature for 30 min. and the solvent was evaporated under reduced pressure. The solid was triturated with ether, collected and dried in vacuo at 80° C. to give (−)-(4S, 2″R)-1′-[(6-cyano-1,2,3,4-tetrahydronaphthalene )-2-yl]-3,4-dihydro-6-methanesulfonamido-4-[2-(phenylsulfonyl)acetamido]spiro(2H-1-benzopyran-2,4′-piperidine) hydrochloride as a colorless solid (72 mg), m.p. >290° C., [α]$_d$ −3.9° (c=0.128, NaOH-H$_2$O/MeOH).

δH(d$_6$-DMSO) 10.7 (1H, br s), 9.44 (1H, s), 8.78 (1H, d, J 8.1 Hz), 7.93–7.59 (7H, m), 7.35 (1H, d, J 8.3 Hz), 7.06 (2H, m), 6.90 (1H, d, J 8.3 Hz), 4.96 (1H, m), 4.33 (2H, m), 3.75–2.80 (9H, m), 2.91 (3H, s), and 2.45–1.60 (8H, m).

Elemental analysis for C$_{33}$H$_{36}$N$_4$O$_6$S$_2$.HCl.1.15H$_2$O:
Calculated; C 56.14; H 5.61; N 7.94%.
Found; C 56.13; H 5.38; N 8.04%.

EXAMPLE 2

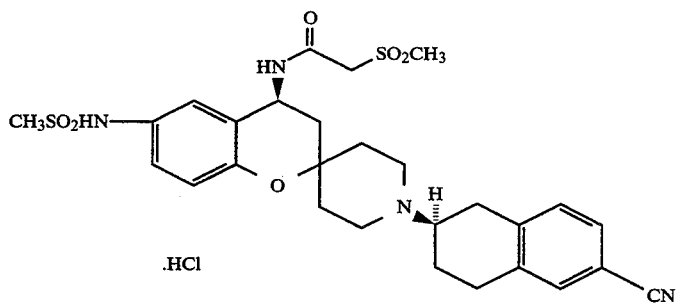

(−)-(4S,
2″R)-1′-[(6-Cyano-1,2,3,4-tetrahydronaphthalene)-2-yl]-3,4-dihydro-6-methanesulfonamido-4-[2-(methanesulfonyl)acetamido]spiro(2H-1-benzopyran-2,4′-piperidine) hydrochloride 1-(3-Dimethylaminopropyl)-3-ethylcarbodiimide hydrochloride (84 mg, 0.44 mmol) was added to a stirred, cooled (0° C.) solution of (4S, 2″R)-1′-[(6-cyano-1,2,3,4-tetrahydronaphthalene)-2-yl]-3,4-dihydro-6-methanesulfonamidospiro(2H-1-benzopyran-2,4′-piperidine)-4-amine (186 mg, 0.40 mmol), methanesulfonylacetic acid (61 mg, 0.44 mmol), 1-hydroxybenzotriazole (67 mg, 0.44 mmol) and DMF (4 drops) in methylene chloride (2 mL). The mixture was stirred at room temperature for 18 h., poured into saturated aqueous sodium hydrogen carbonate (30 mL) and extracted with methylene chloride (4×20 mL). The combined organic fractions were washed with brine (20 mL) dried (Na$_2$SO$_4$) and evaporated under reduced pressure. The residue was purified by flash column chromatography on silica gel, eluting with CH$_2$Cl$_2$/MeOH/NH$_3$ (Aq.) (98:2:0.2 increasing to 92:8:0.8) to give a colorless foam (178 mg, 76%). The residue was suspended in ethanol (3 mL) and HCl-EtOH (6M, 1 mL) was added dropwise with stirring. The mixture was refrigerated over night and the solid was collected and dried in vacuo at 80° C. to give (−)-(4S. 2″R )-1′-[(6-cyano-1,2,3,4-tetrahydronaphthalene )-2-yl]-3,4-dihydro-6-methanesulfonamido-4-[2-(methanesulfonyl)acetamido]spiro(2H-1-benzopyran-2,4′-piperidine) hydrochloride as a colorless solid (164 mg), m.p.>260° C., $[\alpha]_d$ −10.0° (c=0.08, HCl-H$_2$O). $\delta$H(d$_6$-DMSO) 10.9 (1H, br s), 9.45 (1H, s), 8.92 (1H, d, J 8.1 Hz), 7.64 (1H, s), 7.60 (1H, d, J 8.1 Hz), 7.35 (1H, d, J 8.1 Hz), 7.07 (2H, m), 6.91 (1H, d, J 9.3 Hz), 5.06 (1H, m), 4.13 (2H, m), 3.80–2.80 (9H, m), 3.16 (3H, s), 2.90 (3H, s), and 2.45–1.75 (SH, m).

Elemental analysis for C$_{28}$H$_{34}$N$_4$O$_6$S$_2$.HCl:
Calculated; C 53.96; H 5.66; N 8.99%.
Found; C 53.89; H 5.60; N 8.78%.

(−)-(4S,
2″R)-1′-[(6-Cyano-1,2,3,4-tetrahydronaphthalene)-2-yl]-3,4-dihydro-6-methanesulfonamido-4-[2-(phenylthio)acetamido]spiro(2H-1-benzopyran-2,4′-piperidine)hydrochloride 1-(3-Dimethylaminopropyl)-3-ethylcarbodiimide hydrochloride (51 mg, 0.26 mmol) was added to a stirred, cooled (0° C.) solution of (4S, 2″R)-1′-[(6-cyano-1,2,3,4-tetrahydronaphthalene)-2-yl]-3,4-dihydro-6-methanesulfonamidospiro(2H-1-benzopyran-2,4′-piperidine)-4-amine (44 mg, 0.24 mmol), thiophenoxyacetic acid (44 mg, 0.26 mmol) and 1-hydroxybenzotriazole (36 mg, 0.24 mmol) in DMF (3 mL). The mixture was stirred at room temperature for 20 h., poured into saturated aqueous sodium hydrogen carbonate (20 mL), diluted with water (10 mL) and extracted with ethyl acetate (3×20 mL). The combined organic fractions were washed with saturated aqueous sodium hydrogen carbonate (4×20 mL), dried (Na$_2$SO$_4$) and evaporated under reduced pressure. The residue was purified by flash column. chromatography on silica gel, eluting with CH$_2$Cl$_2$MeOH/NH$_3$ (Aq.) (96:4:0.4 increasing to 94:6:0.6) to give a colorless foam (95 mg, 64%). The residue was suspended in ethanol (5 mL) and HCl-EtOH (6M, 0.5 mL) was added dropwise with stirring. The mixture was stirred at ambient temperature for 1 h., then refrigerated over night. The solid was collected and dried in vacuo at 50° C. to give (−)-(4S, 2″R)-1′-[(6-cyano-1,2,3,4-tetrahydronaphthalene)-2-yl]-3,4-dihydro-6-methanesulfonamido-4-[2-(phenylthio)acetamido]spiro(2H-1-benzopyran-2,4′-piperidine) hydrochloride as a colorless solid (84 mg), m.p. 271–273° C., $[\alpha]_d$ −23.8° (c=0.101, MeOH).

$\delta$H(d$_6$-DMSO) 10.6 (1H, br s), 9.41 (1H, s), 8.64 (1H, d, J 8.3 Hz), 7.63 (1H, s), 7.59 (1H, d, J 8.0 Hz), 7.39–7.05 (7H, m), 7.04 (1H, s), 6.88 (1H, d J 8.3 Hz), 5.01 (1H, m), 3.80–2.75 (9H, m), 3.69 (2H, s), 2.87 (3H, s), and 2.45–1.70 (8H, m).

EXAMPLE 3

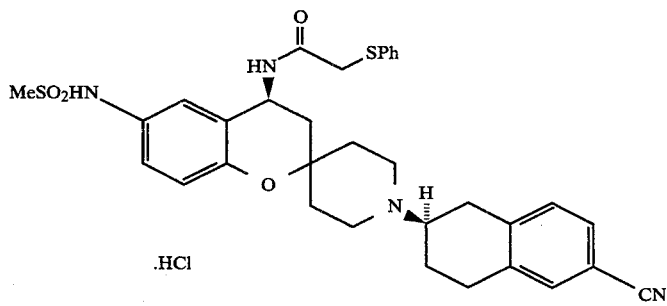

Elemental analysis for $C_{33}H_{36}N_4O_4S_2 \cdot HCl$:
Calculated; C 60.67; H 5.71; N 8.58%.
Found; C 60.63; H 6.03; N 8.62%.

EXAMPLE 4

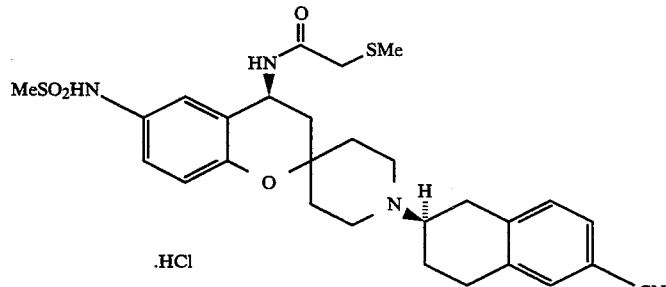

(−)-(4S, 2″R)-1′-[(6-Cyano-1,2,3,4-tetrahydronaphthalene)-2-yl]-3,4-dihydro-6-methanesulfonamido-4-[2-(methylthio)acetamido]spiro(2H-1-benzopyran-2,4′-piperidine)hydrochloride 1-(3-Dimethylaminopropyl)-3-ethylcarbodiimide hydrochloride (109 mg, 0.57 mmol) was added to a stirred, cooled (0° C.) solution of (4S, 2″R)-1′-[(6-cyano-1,2,3,4-tetrahydronaphthalene)-2-yl]-3,4-dihydro-6-methanesulfonamidospiro(2H- 1-benzopyran-2,4′-piperidine)-4-amine (240 mg, 0.52 mmol), methylthioacetic acid (49 μL, 60 mg, 0.57 mmol) and 1-hydroxybenzotriazole (76 mg, 0.52 mmol) in DMF (5 mL). The mixture was stirred at room temperature for 24 h., poured into saturated aqueous sodium hydrogen carbonate (20 mL), diluted with water (10 mL) and extracted with ethyl acetate (3×20 mL). The combined organic fractions were washed with saturated aqueous sodium hydrogen carbonate (4×20 mL), dried ($Na_2SO_4$) and evaporated under reduced pressure. The residue was purified by flash column chromatography on silica gel, eluting with $CH_2Cl_2$/MeOH/$NH_3$ (Aq.) (96:4:0.4 increasing to 90:10:1) to give a colorless foam (149 mg, 52%). A sample (80 mg) was suspended in ethanol (5 mL) and HCl-EtOH (6M, 0.5 mL) was added dropwise with stirring. The mixture was stirred at ambient temperature for 1 h., then refrigerated over night. The solid was collected and dried in vacuo at 60° C. to give (−)-(4S, 2″R)-1′-[(6-cyano-1,2,3,4-tetrahydronaphthalene)-2-yl]-3,4-dihydro-6-methanesulfonamido-4-[2-(methylthio)acetamido]spiro(2H-1-benzopyran-2,4′-piperidine) hydrochloride as a colorless solid (80 mg), m.p. 304–306° C., $[α]_d$ −19.2° (c=0.104, MeOH/10% $H_2O$).

δH($d_6$-DMSO) 10.4 (1H, br s), 9.43 (1H, s), 8.47 (1H, d, J 8.3 Hz), 7.63 (1H, s), 7.60 (1H, d, J 8.1 Hz), 7.34 (1H, d, J 8.1 Hz), 7.04 (2H, m), 6.88 (1H, d, J 9.5 Hz), 5.04 (1H, m), 3.85–2.75 (9H, m), 3.10 (2H, s), 2.88 (3H, s), 2.40–1.70 (8H, m), and 2.14 (3H, s).

Elemental analysis for $C_{28}H_{34}N_4O_4S_2 \cdot HCl \cdot 0.6H_2O$:
Calculated; C 55.86; H 6.06; N 9.31%.
Found; C 55.93; H 5.87; N 9.19%.

EXAMPLE 5

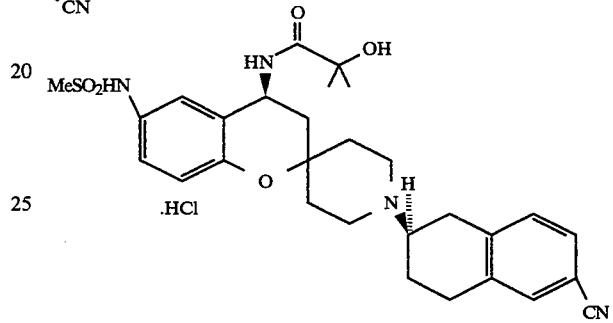

(−)-(4S, 2″R)-1′-[(6-Cyano-1,2,3,4-tetrahydronaphthalene)-2-yl]-3,4-dihydro-4-[(2-hydroxy-2-methyl)propanamido]-6-methanesulfonamidospiro(2H-1-benzopyran-2,4′-piperidine) hydrochloride 1-(3-Dimethylaminopropyl)-3-ethylcarbodiimide hydrochloride (57 mg, 0.30 mmol) was added to a stirred, cooled (0° C.) solution of (4S, 2″R)-1′-[(6-cyano-1,2,3,4-tetrahydronaphthalene)-2-yl]-3,4-dihydro-6-methanesulfonamidospiro(2H- 1-benzopyran-2,4′-piperidine)-4-amine (125 mg, 0.27 mmol), 2-hydroxyisobutyric acid (22 mg, 0.30 mmol) and 1-hydroxybenzotriazole (31 mg, 0.30 mmol) in DMF (4 mL). The mixture was stirred at room temperature for 18 h., poured into saturated aqueous sodium hydrogen carbonate (30 mL) and extracted with ethyl acetate (4×20 mL). The combined organic fractions were washed with brine, dried (MgSO₄) and evaporated under reduced pressure. The residue was purified by flash column chromatography on silica gel, eluting with $CH_2Cl_2$/MeOH/$NH_3$ (Aq.) (95:5:0.5) to give a colorless foam (106 mg, 71%). The residue was suspended in ethanol (1 mL) and HCl-EtOH (6M, 1 mL) was added dropwise with stirring. The mixture was stirred at ambient temperature for 10 min. and the solvent was evaporated under reduced pressure. The solid was triturated with ether then refrigerated for 45 min. The solid was collected and dried in vacuo at 60° C. to give (−)-(4S, 2″R)-1′-[(6-cyano-1,2,3,4-tetrahydronaphthalene)-2-yl]-3,4-dihydro-4-[(2-hydroxy-2-methyl)propanamido]-6-methanesulfonamidospiro(2H-1-benzopyran-2,4′-piperidine) hydrochloride as a colorless solid (88 mg), m.p. 297° C., [α]d −20.0° (c=0.045, $H_2O$).

δH($d_6$-DMSO) 10.6 (1H, br s), 9.45 (1H, s), 8.99 (1H, d, J 8.3 Hz), 7.64 (1H, s), 7.61 (1H, d, J 8.1 Hz), 7.36 (1H, d, J 8.1 Hz), 7.04 (1H, d, J 8.6 Hz), 6.99 (1H, s), 6.86 (1H, d, J 8.6 Hz), 5.38 (1H, s), 5.05 (1H, m), 3.90–2.80 (9H, m), 2.86 (3H, s), 2.45–1.70 (8H, m), 1.34 (3H, s), and 1.29 (3H, s).

Elemental analysis for $C_{29}H_{36}N_4O_5S \cdot HCl \cdot 1.85H_2O$:
Calculated; C 56.04; H 6.44; N 9.02%.
Found; C 56.08; H 6.14; N 8.72%.

EXAMPLE 6

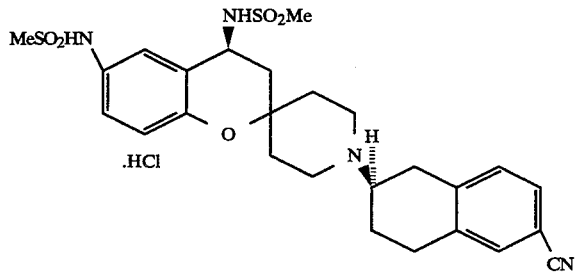

(+)-(4S, 2"R)-1'-[(6-Cyano-1,2,3,4-tetrahydronaphthalene)-2-yl]-3,4-dihydro-4,6-bis(methanesulfonamido)-spiro(2H-1-benzopyran-2,4'-piperidine)hydrochloride Methanesulfonyl chloride (19 μL, 29 mg, 0.28 mmol) was added to a stirred, cooled (0° C.) solution of (4S, 2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (116 mg, 0.25 mmol) in methylene chloride (5 mL). The mixture was stirred at 0° C. for 1 h., then at room temperature for 19 h. Pyridine (40 μL, 40 mg, 0.5 mmol) and methanesulfonyl chloride (19 μL, 29 mg, 0.28 mmol) were added and the mixture was stirred at room temperature for 24 h., poured into saturated aqueous sodium hydrogen carbonate (20 mL), diluted with water (10 mL) and extracted with methylene chloride (3×20 mL). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (94:6:0.6) to give a pale yellow solid (112 mg, 82%). The residue was dissolved in ethanol (5 mL) and HCl-EtOH (6M, 0.5 mL) was added dropwise with stirring. The mixture was stirred at ambient temperature for 1 h., then refrigerated over night. The solid was collected and dried in vacuo at 60° C. to give (+)-(4S, 2"R)-1'-[(6-cyano-1,2,3,4-tetrahydronaphthalene )-2-yl]-3,4-dihydro-4,6-bis(methanesulfonamido)spiro(2H-1-benzopyran-2,4'-piperidine) hydrochloride as a colorless solid (91 mg), m.p. 275–277° C., $[\alpha]_d$ +4.4° (c=0.114, MeOH).

δSH(d_6-DMSO) 10.5 (1H, br s), 9.46 (1H, s), 7.69 (1H, d, J 8.8 Hz), 7.63 (1H, s), 7.59 (1H, d, J 8.2 Hz), 7.34 (1H, d, J 8.2 Hz), 7.31 (1H, s), 7.06 (1H, d, J 8.7 Hz), 6.85 (1H, d, J 8.7 Hz), 4.56 (1H, m), 3.90–2.75 (9H, m), 3.09 (3H, s), 2.89 (3H, s), and 2.40–1.75 (8H, m).

Elemental analysis for $C_{26}H_{32}N_4O_5S_2 \cdot HCl \cdot 1.0.4H_2O$:
Calculated; C 53.07; H 5.79; N 9.52%.
Found; C 53.05; H 5.64; N 9.58%.

EXAMPLE 7

IN VITRO TEST FOR CLASS III ANTIARRHYTHMIC ACTIVITY PURPOSE

This in vitro assay is designed to assess possible potassium channel blocking activity of a compound based on its ability to prolong effective refractory period (ERP) in isolated papillary muscle.

TISSUE PREPARATION

Ferrets (700 to 1200 grams) are anesthetized with 0.7 mL of a mixture of xylazine and ketamine HCL in 1:7 ratio. Papillary muscles from the right ventricle are quickly excised from the isolated heart and mounted in 50 mL organ baths containing Krebs-Henseleit solution (pH=7.2–7.4) at 37° C. The composition of the solution in millimoles per liter are as follows: NaCl, 118; KCl, 4.7; $Na_2CO_3$, 23; $CaCl_2 \cdot 2H_2O$, 2; $MgSO_4 \cdot 7H_2O$, 1.2; $KH_2PO_4$, 1.2; Dextrose, 11.1. Timolol ($10^{-7}M$) is added to the solution to block the effects of released catecholamines during stimulation of the muscles. This solution is aerated with 95% $O_2$ and 5% $CO_2$. The tissue is stimulated at 1 Hz at one msec pulse duration by a square wave stimulator at a voltage 30% above the threshold through platinum electrodes that touch the tissue just above the bottom attachment point. The tendenous end of the tissue is connected by thread to an isometric force transducer leading to a polygraph.

EFFECTIVE REFRACTORY PERIOD (ERP) MEASUREMENT

The ERP is determined by a standard 2 pulse protocol. Both pulses are stimulated at 1.3×voltage threshold. While pacing the tissue at a basal frequency of 1 Hz, a single extra stimulus is delivered after a variable time delay. The shortest delay resulting in a propagated response is defined as the ERP.

PROTOCOL

1. Tissues are mounted with a resting tension of 0.5 gms, stimulated at 1 Hz, and allowed to equilibrate for 2 hours with washings at 15–20 minute intervals.
2. Voltage is adjusted to 30% above threshold and resting tension is adjusted for maximum developed reequilibration time.
3. Effective refractory period is measured at 1 Hz. Changes in resting tension and developed force are noted.
4. After equilibration, ERP's and developed force are measured at 30 minutes following the addition of increasing cumulative concentrations for test agent to the organ bath. Four to five concentrations of test agents were used to generate a concentration-response curve.
5. Four tissues per compound are tested.

RESULTS

Employing the above protocol, it has been found that the effective concentration of most of the compounds of this invention required to increase the refractory period by an increment of 25% above base-line is less than or equal to 10 micromolar, i.e. $EC_{25}$ less than or equal to 10 micromolar, whereas sotalol in the same protocol has an $EC_{25}$ of approximately 20 micromolar.

EXAMPLE 8

PREPARATION OF INTRAVENOUS SOLUTIONS

A solution containing 0.5 mg of active ingredient per mL of injectable solution is prepared in the following manner:

A mixture of 0.5 mg of active ingredient is dissolved in 1 mL of acetate buffer. The pH is adjusted using hydrochloric acid or aqueous sodium hydroxide to about pH 5.5. If it is desired that the intravenous solution be used for multi-dose purposes, 1.0 mg of methylp-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.001, 0.01 and 0.1 mg, respectively, of active ingredient per mL of solution are similarly prepared substituting the indicated amount for the above-illustrated 10 mg quantity. Bulk injectable solutions of convenient volume for subsequent delivery in unit dosage form are readily prepared following the above procedure.

EXAMPLE 9

TABLET PREPARATION

Tablets containing 0.1, 1.0, 2.0, 25, 26.0, 50.0 and 100.0 mg, respectively, of active ingredient are prepared as illustrated below.

| TABLE FOR DOSES CONTAINING FROM 0.1-25 mg OF THE ACTIVE COMPOUND Amount in mg | | | | |
|---|---|---|---|---|
| Active ingredient | 0.10 | 1.0 | 2.0 | 25.0 |
| Microcrystalline cellulose | 49.70 | 49.25 | 48.75 | 37.25 |
| Modified food corn starch | 49.70 | 49.25 | 48.75 | 37.25 |
| Magnesium stearate | 0.50 | 0.50 | 0.50 | 0.50 |

| TABLE FOR DOSES CONTAINING FROM 26-100 mg OF THE ACTIVE COMPOUND Amount in mg | | | |
|---|---|---|---|
| Active ingredient | 26.0 | 50.0 | 100.0 |
| Microcrystalline cellulose | 25.0 | 100.0 | 200.0 |
| Modified food corn starch | 0.39 | 4.25 | 8.5 |
| Magnesium stearate | 0.39 | 0.75 | 1.50 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 0.1, 1.0 mg, 2.0 mg, 25.0 mg, 26.0 rag, 50 mg, and 100 mg of active ingredient per tablet.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of the structural formulae:

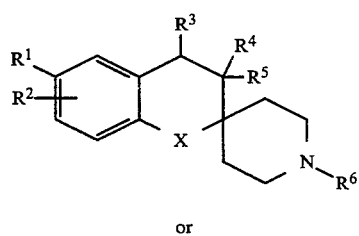

or

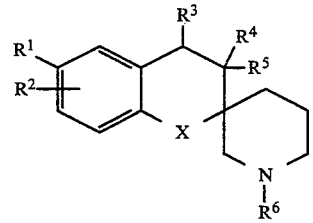

wherein:

X is O, $CH_2$ or $SO_m$;

$R^1$ is $AlkylSO_2NH-$, $AlkylO-$, $AlkylSO_2-$, $AlkylCONH-$, or $NO_2-$;

$R^2$ is $-H$, $-OAlkyl$, or $-Alkyl$;

$R^3$ is $-NHCOCH_2SO_mPhenyl$, $-NHCOCH_2SO_mAlkyl$, or $NHSO_2Alkyl$;

$R^4$ and $R^5$ are $-H$, or $-Alkyl$;

$R^6$ is

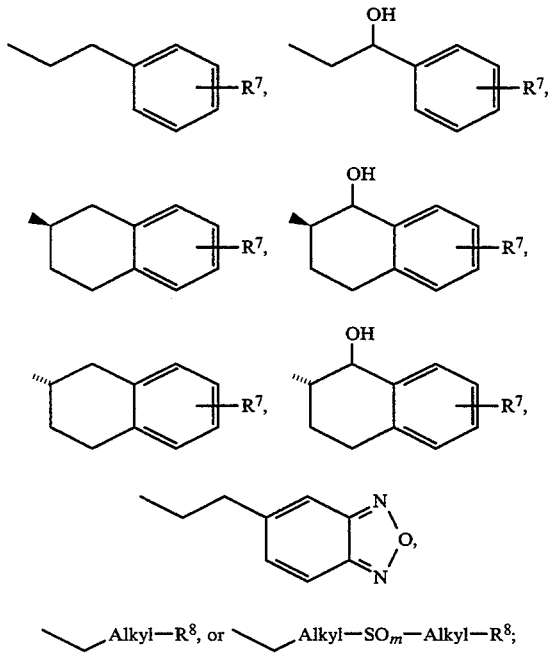

$R^7$ is $-H$, $-CN$, $-NHSO_2Alkyl$, $-Br$, $-OAlkyl$, $-NH_2$, $-NO_2$, $-NHCOAlkyl$, or $NHCONHAlkyl$;

$R^8$ is $-H$, $-OH$, $-CN$, $-OAlkyl$, $-CONHAlkyl$, $-NHSO_2Alkyl$, $-NHCOAlkyl$, $-SO_mAlkyl$, or $-CO_2Alkyl$;

and m is 0–2; or a pharmaceutically acceptable salt, hydrate or crystal form thereof.

2. The compounds of the formulae of claim 1, wherein:

X is O;

$R^1$ is $AlkylSO_2NH-$, $AlkylO-$, $AlkylSO_2-$, $AlkylCONH-$, or $NO_2-$;

$R^2$ is $-H$, $-OAlkyl$, or $-Alkyl$;

$R^3$ is $-NHCOCH_2SO_mPhenyl$, $-NHCOCH_2SO_mAlkyl$, or $NHSO_2Alkyl$;

$R_4$ and $R_5$ are $-H$ or $-Alkyl$;

$R^6$ is

R⁷ is —H, —CN, —NHSO₂Alkyl, —Br, —OAlkyl, —NH₂, —NO₂, —NHCOAlkyl, or NHCONHAlkyl;

R⁸ is —H, —OH, —CN, —OAlkyl, —CONHAlkyl, —NHSO₂Alkyl, —NHCOAlkyl, —SO$_m$Alkyl, or —CO₂Alkyl;

and m is 0–2; or a pharmaceutically acceptable salt, hydrate or crystal form thereof.

3. The compounds of the formulae of claim 1, wherein:

X is CH₂;
R₁ is AlkylSO₂NH—, AlkylO—, AlkylSO₂—, AlkylCONH—, or NO₂—;
R₂ is —H, —OAlkyl, or —Alkyl;
R₃ is —NHCOCH₂SO$_m$Phenyl, —NHCOCH₂SO$_m$Alkyl, or NHSO₂Alkyl;
R₄ and R₅ are —H or —Alkyl;
R₆ is R⁷ is —H, —CN, —NHSO₂Alkyl, —Br, —OAlkyl, —NH₂, —NO₂, —NHCOAlkyl, or NHCONHAlkyl;

R⁸ is —H, —OH, —CN, —OAlkyl, —CONHAlkyl, —NHSO₂Alkyl, —NHCOAlkyl, —SO$_m$Alkyl, or —CO₂Alkyl;

and m is 0–2; or a pharmaceutically acceptable salt, hydrate or crystal form thereof.

4. The compounds of the formulae of claim 1, wherein:

X is SO$_m$;
R₁ is AlkylSO₂NH—, AlkylO—, AlkylSO₂—, AlkylCONH—, or NO₂—;
R₂ is —H, —OAlkyl, or —Alkyl;
R₃ is —NHCOCH₂SO$_m$Phenyl, —NHCOCH₂SO$_m$Alkyl, or NHSO₂Alkyl;
R₄ and R₅ are —H or —Alkyl;
R₆ is R⁷ is —H, —CN, —NHSO₂Alkyl, —Br, —OAlkyl, —NH₂, —NO₂, —NHCOAlkyl, or NHCONHAlkyl;

R⁸ is —H, —OH, —CN, —OAlkyl, —CONHAlkyl, —NHSO₂Alkyl, —NHCOAlkyl, —SO$_m$Alkyl, or —CO₂Alkyl;

and m is 0–2; or a pharmaceutically acceptable salt, hydrate or crystal form thereof.

5. The compounds of the formulae of claim 1, wherein

X is O;
R¹ is H₃CSO₂NH—;
R² is —H;
R³ is —NHCOCH₂SO$_m$Phenyl, —NHCOCH₂SO$_m$Alkyl, or NHSO₂Alkyl;
R⁴ and R⁵ are —H;
and R⁶ is

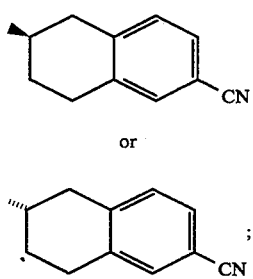

or

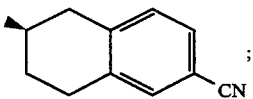

or a pharmaceutically acceptable salt, hydrate or crystal form thereof.

6. The compounds of the formula of claim 1, wherein:
X is O;
R$^1$ is H$^3$CSO$_2$NH—;
R$^2$ is —H;
R$^3$ is —NHCOCH$_2$SO$_m$Phenyl, —NHCOCH$_2$SO$_m$Alkyl, or NHSO$_2$Alkyl;
R$^4$ and R$^5$ are —H;
and R$^6$ is

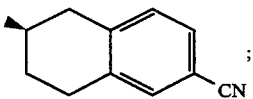

or a pharmaceutically acceptable salt, hydrate or crystal form thereof.

7. A compound selected from the group consisting of:

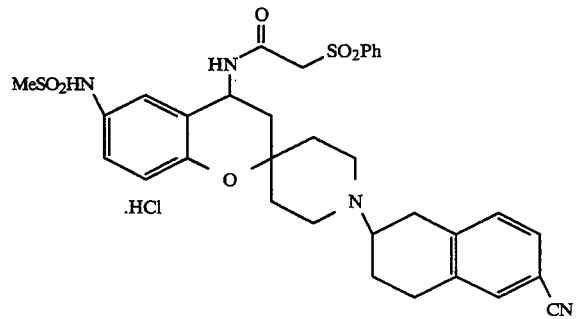

1'-[(6-Cyano-1,2,3,4-tetrahydronaphthalene)-2-yl]-3,4-dihydro-6-methanesulfonamido-4-[2-(phenylsulfonyl)acetamido]spiro(2H- 1-benzopyran-2,4'-piperidine);

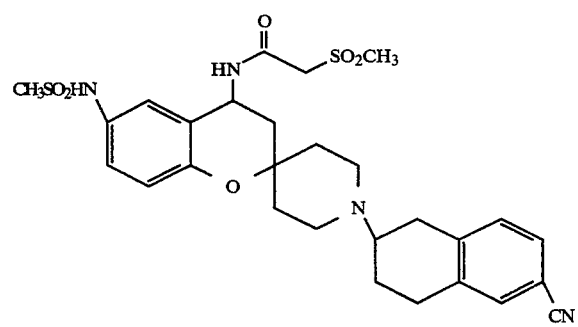

1'-[(6-Cyano-1,2,3,4-tetrahydronaphthalene)-2-yl]-3,4-dihydro-6-methanesulfonamido-4-[2-(methanesulfonyl)acetamido]spiro(2H-1-benzopyran-2,4'-piperidine);

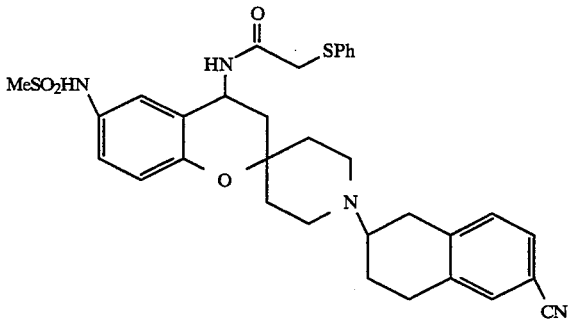

1'-[(6-Cyano-1,2,3,4-tetrahydronaphthalene)-2-yl]-3,4-dihydro-6-methanesulfonamido-4-[2-(phenylthio)acetamido]spiro(2H- 1-benzopyran-2,4'-piperidine);

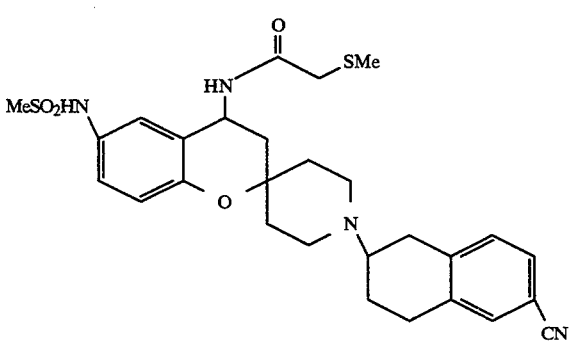

1'-[(6-Cyano-1,2,3,4-tetrahydronaphthalene)-2-yl]-3,4-dihydro-6-methanesulfonamido-4-[2-(methylthio)acetamido]spiro(2H- 1-benzopyran-2,4'-piperidine);

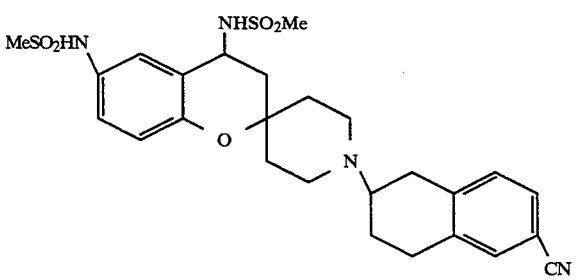

1'-[(6-Cyano-1,2,3,4-tetrahydronaphthalene)-2-yl]-3,4-dihydro-4,6-bis(methanesulfonamido)spiro(2H-1-benzopyran-2,4'-piperidine);

as diastereomers and enantiomers, or mixtures thereof, or pharmaceutically acceptable salts, hydrates or crystal forms thereof.

8. A compound selected from the group consisting of:

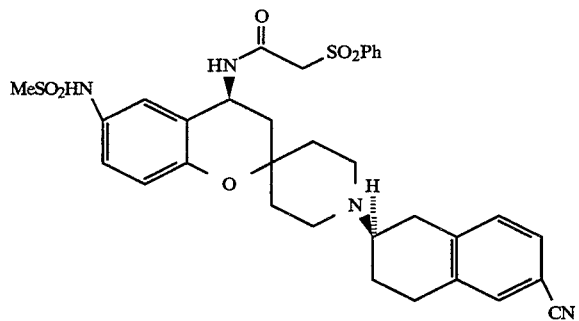

(4S, 2″R)-1'-[(6-Cyano-1,2,3,4-tetrahydronaphthalene)-2-yl]-3,4-dihydro-6-methanesulfonamido-4-[2-(phenylsulfonyl)acetamido]spiro(2H-1-benzopyran-2,4'-piperidine);

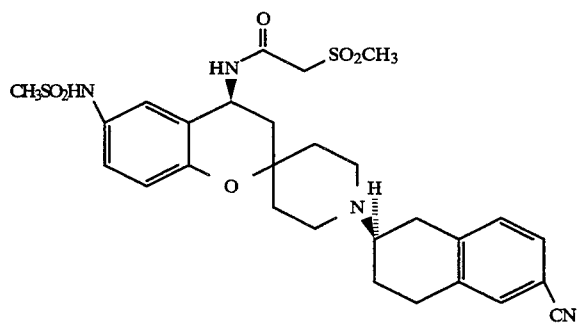

(4S, 2″R)- 1'-[(6-Cyano-1,2,3,4-tetrahydronaphthalene)-2-yl]-3,4-dihydro-6-methanesulfonamido-4-[2-(methanesulfonyl)acetamido]spiro(2H-1-benzopyran-2,4'-piperidine);

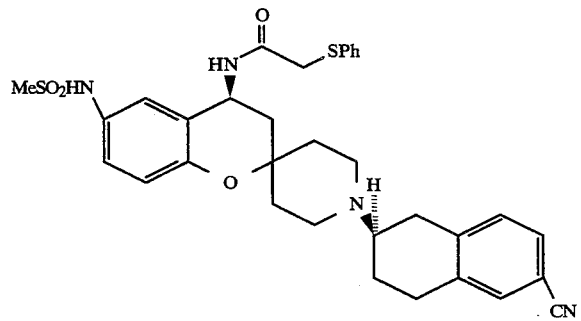

(4S, 2″R)-1'-[(6-Cyano-1,2,3,4-tetrahydronaphthalene)-2-yl]-3,4-dihydro-6-methanesulfonamido-4-[2-(phenylthio)acetamido]spiro(2H-1-benzopyran-2,4'-piperidine);

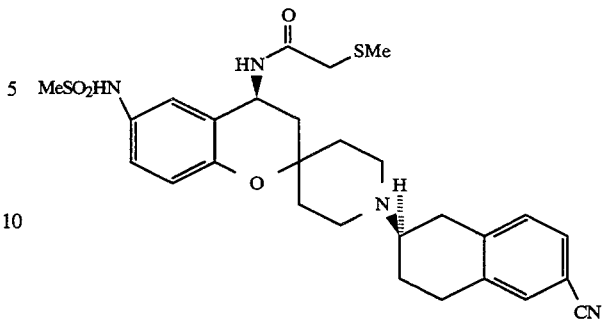

(4S, 2″R )-1'-[(6-Cyano-1,2,3,4-tetrahydronaphthalene)-2-yl]-3,4-dihydro-6-methanesulfonamido-4-[2-(methylthio)acetamido]spiro(2H-1-benzopyran-2,4'-piperidine);

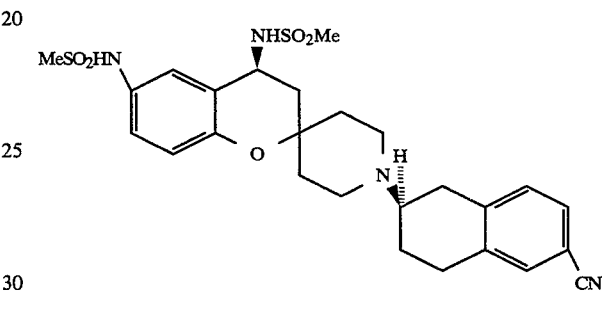

(4S, 2″R)-1'-[(6-Cyano-1,2,3,4-tetrahydronaphthalene)-2-yl]-3,4-dihydro-4,6-bis(methanesulfonamido)spiro(2H- 1-benzopyran-2,4'-piperidine);
or pharmaceutically acceptable salts, hydrates or crystal forms thereof.

9. A pharmaceutical formulation comprising a carrier and a therapeutically effective amount of a compound of claim 1.

10. The pharmaceutical formulation of claim 9, wherein the pharmaceutically effective amount of compound ranges from about 0.0001 to about 20 mg per kg of body weight per day.

11. A method of treating arrhythmia in a patient in need of such treatment which comprises administering to such patient a therapeutically effective amount of the compound of claim 1.

12. The method of claim 11, wherein the therapeutically effective amount of compound is administered orally, intraperitoneally, subcutaneously, intramuscularly, transdermally, sublingually or intravenously.

13. The method of claim 11, wherein the therapeutically effective amount of compound is administered orally or intravenously.

* * * * *

UNITED STATES PATENT AND TRADEMARK OFFICE
CERTIFICATE OF CORRECTION

PATENT NO. : 5,382,587            Page 1 of 2
DATED : January 17, 1995
INVENTOR(S) : John J. Baldwin, David A. Claremon and Jason M. Elliott It is certified that error appears in the above-indentified patent and that said Letters Patent is hereby corrected as shown below:

At Column 33, in claim 6, please replace line 18,
which reads "$R^1$ is $H^3CSO_2NH-$;"
with -- $R^1$ is $H_3CSO_2NH-$; --.

At Column 34, in claim 7, please replace line 22,
which reads "thio)acetamido]spiro(2H-   1-benzopyran-2,4'-"
with -- thio)acetamido]spiro(2H-1-benzopyran-2,4'- --.

At Column 34, in claim 7, please replace line 43,
which reads "thio)acetamido]spiro(2H-   1-benzopyran-2,4'-"
with -- thio)acetamido]spiro(2H-1-benzopyran-2,4'- --.

At Column 35, in claim 8, please replace line 16,
which reads "(4S,   2"R)-1'-[(6-Cyano-1,2,3,4-tetrahydronaph-"
with -- (4S,2"R)-1'-[(6-Cyano-1,2,3,4-tetrahydronaph- --.

UNITED STATES PATENT AND TRADEMARK OFFICE
CERTIFICATE OF CORRECTION

PATENT NO. : 5,382,587
DATED : January 17, 1995
INVENTOR(S) : John J. Baldwin, David A. Claremon and Jason M. Elliott It is certified that error appears in the above-indentified patent and that said Letters Patent is hereby corrected as shown below:

At Column 35, in claim 8, please replace line 52,
which reads "(4S,     1'-[(6-Cyano-1,2,3,4-tetrahydronaph-"
with -- 4S,2"R)-1'-[(6-Cyano-1,2,3,4-tetrahydronaph- --.

At Column 36, in claim 8. please replace line 16,
which reads (4S,    2"R   )-1'-[(6-Cyano-1,2,3,4-tetrahydronaph-"
with -- (4S,2"R)-1'-[(6-Cyano-1,2,3,4-tetrahydronaph- --.

At Column 36, in claim 8, please replace line 32,
which reads (4S,     2"R)-1'-[(6-Cyano-1,2,3,4-tetrahydronaph-"
with (4S,2"R)-1'-[(6-Cyano-1,2,3,4-tetrahydronaph- --.

Signed and Sealed this

Eighth Day of August, 1995

Attest:

BRUCE LEHMAN

*Attesting Officer*                *Commissioner of Patents and Trademarks*